United States Patent [19]

Van Broekhoven et al.

[11] 4,297,517
[45] Oct. 27, 1981

[54] PREPARATION OF CARBONYL COMPOUNDS FROM ALLYLETHERS

[75] Inventors: Johannes A. M. Van Broekhoven; Eit Drent, both of Amsterdam, Netherlands

[73] Assignee: Shell Oil Company, Houston, Tex.

[21] Appl. No.: 174,074

[22] Filed: Jul. 31, 1980

[30] Foreign Application Priority Data

Sep. 4, 1979 [GB] United Kingdom ............... 30594/79

[51] Int. Cl.$^3$ .................... C07C 45/59; C07C 45/42
[52] U.S. Cl. ............................ 568/361; 260/346.11; 568/483; 568/485; 568/489; 568/907
[58] Field of Search ............... 260/346.11; 568/361, 568/483, 485, 489, 907

[56] References Cited

U.S. PATENT DOCUMENTS 2,533,172 12/1950 McKinley .......................... 568/485
2,662,919 12/1953 Hagemeyer et al. ........... 568/485 X Primary Examiner—Richard Raymond

[57] ABSTRACT

A process for hydrolysing allylethers of the general formula:

$$R_6CH=CR_5-CR_4-O-CR_1R_2R_3$$

wherein $R_1$, $R_2$, $R_3$, $R_4$, $R_5$ and $R_6$, which may be the same or different, represent a hydrogen atom or an alkyl group of from 1 to 8 carbon atoms or one of $R_1$, $R_2$ or $R_3$ and $R_6$ together represent a covalent bond, with water in the presence of a supported Group VIII metal catalyst. Methyl sec-butenyl ether can be hydrolysed in high yield to methyl ethyl ketone.

11 Claims, No Drawings

PREPARATION OF CARBONYL COMPOUNDS FROM ALLYLETHERS

FIELD OF THE INVENTION

This invention relates to a process for hydrolysing allylethers to give the corresponding ketones or aldehydes utilizing a supported Group VIII metal catalyst.

BACKGROUND OF THE INVENTION

The present invention provides a process for hydrolysing allylethers to give carbonyl compounds, particularly for hydrolysing alkyl sec-butenyl ethers to give methyl ethyl ketone and the corresponding alkanol. Ketones are of great importance as solvents as well as starting materials for chemical syntheses. Aldehydes are of interest as such and can also be used as intermediate in chemical syntheses.

Although the hydrolysis of vinylethers is known in the art, e.g. from U.S. Pat. No. 2,622,919 issued Jan. 26, 1960 describing the use of a supported silver oxide catalyst at temperature between 220° C. and 300° C. to give aldehydes and alkanols and from U.S. Pat. No. 2,533,172 issued Dec. 5, 1950 describing the use of a supported acidic catalyst at temperatures of at least 150° C. to give aldehydes and alkanols, no reference is made to the hydrolysis of allylethers. Moreover, it was determined experimentally that the hydrolysis of methyl sec-butenyl ether under acidic conditions gives butadiene and methanol as major products (<90%) and a small amount of isomeric butenols.

SUMMARY OF THE INVENTION

The instant process has been found to hydrolyse allylethers under mild process conditions to give in high yield the corresponding ketones or aldehydes when using a supported Group VIII metal catalyst. Preferably the catalytic metal is selected from the group consisting of platinum, palladium, rhodium, and iridium, preferably palladium and platinum. The presence of more than one metal, say palladium and platinum is beneficial and causes very high conversions and selectivities. Preferred carriers are aluminum oxides, especially gamma-aluminas.

DESCRIPTION OF THE PREFERRED EMBODIMENTS

The present invention therefore relates to a process for hydrolysing allylethers of the general formula:

$$R_6CH=CR_5-CR_4H-O-CR_1R_2R_3 \qquad (I)$$

wherein $R_1$, $R_2$, $R_3$, $R_4$, $R_5$ and $R_6$, which may be the same or different, represent a hydrogen atom or an alkyl group of from 1 to 8 carbon atoms or one of $R_1$, $R_2$ or $R_3$ and $R_6$ together represent a covalent bond, which comprises reacting at least one allylether according to the general formula I with water in the presence of a supported Group VIII metal catalyst.

When acyclic allylethers, i.e. compounds wherein $R_6$ does not form a covalent bond with one of $R_1$, $R_2$ or $R_3$, are hydrolysed according to the process according to the present invention aldehydes or ketones and the corresponding alkanols are formed whereas the hydrolysis of cyclic allylethers leads to the production of hydroxyaldehydes or ketones which can e.g. be hydrogenated to give diols.

Preference is given to the use of allylethers according to the general formula I wherein $R_1$, $R_2$ and $R_3$ which may be the same or different represent a hydrogen atom or an alkyl group of from 1 to 4 carbon atoms; $R_4$ represents an alkylgroup of up to 4 carbon atoms; $R_5$ represents a hydrogen atom or an alkyl group of from 1 to 8 carbon atoms; $R_6$ represents a hydrogen atom or an alkyl group of from 1 to 8 carbon atoms or one of $R_1$, $R_2$ or $R_3$ and $R_6$ together represent a covalent bond.

More preferred allylethers to be used in the process according to the present invention are those according to the general formula I wherein $R_1$, $R_2$ and $R_3$ which may be the same or different represent a hydrogen atom or a methyl group; $R_4$ represents a methyl or ethyl group; $R_5$ represents a hydrogen atom or a methyl or ethyl group; $R_6$ represents a hydrogen atom or an alkyl group of from 1 to 4 carbon atoms or one of $R_1$, $R_2$ or $R_3$ and $R_6$ together represent a covalent bond.

Very good results have been obtained using methyl sec-butenyl ether or 2,5-dihydrofuran as the starting materials for the preparation of methyl ethyl ketone (and methanol) and gamma-hydroxy butyraldehyde, respectively.

The process according to the present invention can be conveniently carried out using a supported Group VIII metal catalyst. Preferred metals of Group VIII of the Periodic Table of the Elements comprise platinum, palladium, rhodium and iridium, most preference being given to the use of palladium and platinum. The amount of Group VIII metal to be used in the process according to the present invention can be varied within wide limits. Amounts as low as 0.05% can be used, preference being given to amounts in the range of from about 0.1 to about 10%, calculated on support. Higher amounts of Group VIII metals can be used but they do not give substantially better results than the amounts indicated. Very good results have been obtained using palladium in an amount between about 0.1 and about 2%, calculated on support.

It has been found that the presence of a further Group VIII metal may have a beneficial effect on the hydrolysis of the allylethers according to the present invention. The presence of both platinum and one of paladium, rhodium or iridium in the catalytic system may substantially enhance the conversion of the allylethers according to the general formula I. Especially the presence of both platinum and palladium in catalytic system causes very high conversions and selectivities. The ratio of the metals present in such bimetallic catalytic systems may vary within wide limits. Ratios of platinum/further Group VIII metal in the range of from about 20:1 to about 1:20 can be suitably employed, preference being given to ratios of from about 5:1 to about 1:2.

The support can be chosen from a great many porous carrier materials which are essentially inert vis a vis the reaction mixture under the appropriate reaction conditions. The carrier material may be inorganic or organic and of synthetic or natural origin. Suitable carrier materials are for instance those comprising oxygen compounds of silicon and/or aluminum.

Examples of suitable carrier materials comprise aluminum-oxides, i.e. materials such as ALUNDUM (the word ALUNDUM is a registered Trade Mark), aluminum silicates, for instance kaolinites, montmorilonites and micas, pumice, magnesium oxide, zirconium oxide, zirconium silicate, diatomaceous earth, fuller's earth, silicon carbide, porous agglomerates containing silicon carbide, silicon dioxide, clays, synthetic and natural zeolites such as mordenite and ceramic materials.

Preferred carriers to be used in the process according to the present invention comprise aluminum oxides, expecially gamma-aluminas.

It has been found advantageous to subject the supported catalyst material to a reducing treatment prior to use in the reaction. A suitable reducing treatment comprises heating the supported catalyst material in a hydrogen containing atmosphere at elevated temperatures e.g. temperatures between about 100° C. and about 500° C. It may be advantageous to treat the surface of the carrier with alkali or alkaline earth metal ions prior to impregnating the metal compound or to subject the reduced supported catalyst material to an alkaline wash treatment, e.g. by washing the reduced supported catalyst with an aqueous solution of a base such as sodium hydroxide or potassium hydroxide. This will normally cause the incorporation of alkali or earth alkaline metal ions in the supported catalyst materials. Amounts up to about 10%w, based on total catalyst, or even higher amounts can be used. The presence of sodium ions in the range of from about 0.5% to about 2% by weight is preferred for practical reasons.

The ratio allylether according to the general formula I/water is not critical and may vary within wide limits. Normally, a molar excess of water will be used, e.g. molar ratios in excess of about 10, and even as high as 100 can be used. Preference is given to ratios in the range of from about 1 to about 60.

If desired, the process according to the present invention may be carried out in the presence of an inert solvent which facilitates the mixing of the alkyl butenyl ether and water. Suitable solvents comprise lower alkanols such as methanol, ethanol and isopropanol as well as lower ketones such as acetone, methyl ethyl ketone and methyl isopropylketone. The amount of solvent to be applied is not critical and may vary within wide limits. Good results can be obtained using a solvent-/reactants weight ratio of from about 1 to about 50. It should be noted that applying higher amounts of water in the process according to the present invention reduces the desirability to have a (further) solvent present.

The process according to the present invention may be carried out at elevated temperatures, e.g. at about 40° C. and is particularly suitable for hydrolysis reactions at temperatures of above about 80° C., e.g. from about 90° C. to about 160° C. The reaction pressure is such as to maintain the solvent, if any and water in the liquid state. The allylether may be in the liquid or gaseous state (trickle flow operation). Suitable reaction pressures are in the range of from about 1 to about 200 bar, preferably from about 10 to about 100 bar, most preferably from about 20 to about 50 bar.

The reaction product may be worked up by techniques known in the art. The reaction product mixture may be subjected to a fractional distillation to separate the various components in the product mixture. Normally the various fractions will be obtained in the form of the appropriate azeotropic mixtures such as for intance when methyl ethyl ketone is the reaction product, a methyl ethyl ketone/water azeotrope may be formed. The azeotropes may be split by methods known in the art. A convenient method comprises a further distillation using benzene or cyclohexane.

Allylethers which can be used as starting materials in the process according to the present invention can be conveniently prepared by a process described in out copending application Ser. No. 171,685, filed July 24, 1980 which comprises reacting a conjugated diene and a lower alkanol with the aid of an acidic catalyst in the presence of a non-basic aprotic polar solvent. Thus, methyl sec-butenyl ether to be used as the starting material for the hydrolysis according to the present invention giving methyl ethyl ketone and methanol, can be conveniently prepared by reacting butadiene with methanol with the aid of an acidic catalyst, preferably an acidic ion-exchange resin in the presence of sulpholane.

The present invention will be illustrated by means of the following Examples which are provided for illustration and are not to be construed as limiting the invention. The experiments described in the Examples I-VI were carried out using a 20 cc electrically heated tubular reactor under full liquid operation. The experiments were carried out using a large excess of water and/or ethanol to ensure one homogeneous liquid phase under the reaction conditions. The catalysts employed were prepared by impregnating a Group VIII-metal salt solution on an inert carrier followed by drying and reducing the metal-ion thus impregnating in a hydrogen atmosphere at elevated temperature. The reduced catalytic material was subjected to a wash treatment using an aqueous alkali solution (Examples I and II), whereas in the Examples III-V and VII the carrier material contained the indicated amount of sodium ions.

EXAMPLE I

One percent by weight (pbw) of methyl sec-butenyl ether, 10 pbw of water and 9 pbw of ethanol were passed at a total hourly space velocity of 0.6 kg.kg$^{-1}$.h$^{-1}$ at a temperature of 100° C. and at a pressure of 30 bar through the electrically heated tubular reactor containing 0.3% w of palladium and 0.2% w of platinum on 10 g mordenite (H+). The reduced catalyst had been washed with an aqueous solution of ca. 10% sodium hydroxide at room temperature. The conversion to methyl ethyl ketone and methanol amounted to 25% as determined by gas-liquid chromotography and calculated on starting material.

EXAMPLE II

The experiment described in Example I was repeated using gamma-alumina as the support containing 0.5% w of palladium and 0.5% w of platinum. The reduced catalyst had been washed with an aqueous solution of ca. 10% sodium hydroxide. The conversion to methyl ethyl ketone and methanol amounted to 78% calculated on starting material.

EXAMPLE III

One pbw of methyl sec-butenyl ether and 9 pbw of water were passed at a total hourly space velocity of 1.6 kg.kg$^{-1}$.h$^{-1}$ at a temperature of 120° C. and at a pressure of 30 bar through the electrically heated tubular reactor containing 0.5% w of palladium and 0.5% w platinum on gamma-alumina containing 1.5% w sodium-ion. The conversion to methyl ethyl ketone and methanol amounted to 83% calculated on starting material.

EXAMPLE IV

The experiment described in Example III was repeated using 0.25% w of rhodium instead of platinum. The gamma-alumina contained 1.6% w of sodium-ion.

The conversion of methyl ethyl ketone and methanol amounted to 52% calculated on starting material.

EXAMPLE V

The experiment described in Example IV was repeated using 0.5% w of iridium instead of rhodium. The conversion to methyl ethyl ketone and methanol amounted to 40% calculated on starting material.

EXAMPLE VI

The experiment described in Example III was repeated using a gamma-alumina (Baker D) catalyst containing 0.5% w of palladium. The conversion to methyl ethyl ketone and methanol amounted to 94% calculated on starting material.

EXAMPLE VII

A 300 ml stirred Hastelloy C autoclave was charged with 16 g 2,5-dihydrofuran, 80 g water and 5 g of the catalyst described in Example III. The autoclave was heated for 3 hours at 120° C. After cooling the resulting liquid was analysed by means of gas-liquid chromatography. The conversion of 2,5-dihydrofuran amounted to 55% gamma-hydroxy butyraldehyde having been formed with a selectivity of 65%. 2,3-Dihydrofuran, tetrahydrofuran and furan had also been formed in minor amounts.

What is claimed is:

1. A process for hydrolysing allylethers of the general formula:

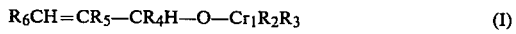

$$R_6CH=CR_5-CR_4H-O-Cr_1R_2R_3 \quad (I)$$

wherein $R_1$, $R_2$, $R_3$, $R_4$, $R_5$ and $R_6$, which may be the same or different, represent a hydrogen atom or an alkyl group of from 1 to 8 carbon atoms or one of $R_1$, $R_2$ or $R_3$ and $R_6$ together represent a covalent bond, which comprises reacting at least one allylether according to the general formula I with water in the presence of a supported Group VIII metal catalyst selected from the group consisting of platinum, palladium, rhodium and iridium.

2. The process of claim 1, wherein an allylether according to the general formula I is used in which $R_1$, $R_2$ and $R_3$ which may be the same or different represent a hydrogen atom or an alkyl group of from 1 to 4 carbon atoms; $R_4$ represents an alkyl group of up to 4 carbon atoms; $R_5$ represents a hydrogen atom or an alkyl group of from 1 to 8 carbon atoms; $R_6$ represents a hydrogen atom or an alkyl group of from 1 to 8 carbon atoms or one of $R_1$, $R_2$ or $R_3$ and $R_6$ together represents a covalent bond.

3. The process of claim 2, wherein an allylether according to the general formula I is used in which $R_1$, $R_2$ and $R_3$ which may be the same or different represent a hydrogen atom or a methyl group; $R_4$ represents a methyl or ethyl group; $R_5$ represents a hydrogen atom or a methyl or ethyl group; $R_6$ represents a hydrogen atom or an alkyl group of from 1 to 4 carbon atoms or one of $R_1$, $R_2$ or $R_3$ and $R_6$ together represent a covalent bond.

4. The process of claim 3, wherein the allylether used in methyl sec-butenyl ether or 2,5-dihydrofuran.

5. The process of claim 1 wherein the amount of metal catalyst employed is from about 0.05 to about 10 percent by weight, calculated on the support.

6. The process of claim 5 wherein the amount of metal catalyst employed is from about 0.1 to about 2 percent by weight calculated on the support.

7. The process of claim 1 wherein a further Group VIII metal selected from the group consisting of platinum, palladium, rhodium and iridium is also present in the catalyst.

8. The process of claim 7 wherein the catalyst contains both palladium and platinum in a ratio ranging from about 5:1 to about 1:2.

9. The process of claims 1, 2, 3, 4, 5, 6, 7, or 8 wherein the support is gamma-alumina.

10. The process of claims 1, 2, 3, 4, 5, 6, 7, or 8 wherein the support is gamma-alumina additionally containing from about 0.5 to about 2 percent by weight of sodium ions.

11. The process of claims 1, 2, 3, 4, 5, 6, 7, or 8 wherein the reaction is carried out at a temperature of from about 90° C. to about 160° C.

* * * * *